United States Patent
Salce, Jr. et al.

(10) Patent No.: US 10,034,832 B2
(45) Date of Patent: Jul. 31, 2018

(54) SUBLINGUAL ANTIDEPRESSANT LOZENGE

(71) Applicant: SYNERGISTIC THERAPEUTICS, LLC, Naples, FL (US)

(72) Inventors: Anthony H. Salce, Jr., Naples, FL (US); William F. Greenwood, Fairfield, CT (US); Shivsankar Misir, Naples, FL (US)

(73) Assignee: Synergistic Therapeutics, LLC, Naples, FL (US)

( * ) Notice: Subject to any disclaimer, the term of this patent is extended or adjusted under 35 U.S.C. 154(b) by 0 days.

(21) Appl. No.: 15/431,242

(22) Filed: Feb. 13, 2017

(65) Prior Publication Data
US 2017/0231906 A1    Aug. 17, 2017

Related U.S. Application Data

(60) Provisional application No. 62/294,590, filed on Feb. 12, 2016.

(51) Int. Cl.
| | |
|---|---|
| *A61K 9/56* | (2006.01) |
| *A61K 9/00* | (2006.01) |
| *A61K 31/135* | (2006.01) |
| *A61K 9/20* | (2006.01) |
| *A23G 3/36* | (2006.01) |
| *A23G 3/34* | (2006.01) |

(52) U.S. Cl.
CPC .......... *A61K 9/0056* (2013.01); *A23G 3/0053* (2013.01); *A23G 3/364* (2013.01); *A61K 9/2009* (2013.01); *A61K 9/2013* (2013.01); *A61K 31/135* (2013.01); *A23V 2002/00* (2013.01)

(58) Field of Classification Search
CPC ...................................................... A61K 9/53
See application file for complete search history.

(56) References Cited

U.S. PATENT DOCUMENTS

| | | | |
|---|---|---|---|
| 2003/0181528 A1* | 9/2003 | Friedman | A61K 31/135 514/648 |
| 2015/0374770 A1* | 12/2015 | Crowley | A61K 36/185 424/725 |

OTHER PUBLICATIONS

Verma (Journal der Pharmazie Forschung, vol. 2: No. 1: 1-10: 2014).*

* cited by examiner

*Primary Examiner* — Benjamin Packard
(74) *Attorney, Agent, or Firm* — Moritt Hock & Hamroff LLP; Steven S. Rubin, Esq.

(57) ABSTRACT

Technologies are described for formulations and methods to produce sublingual antidepressant lozenges. The lozenges may comprise troche base and ketamine. The lozenges may comprise 0.35 weight percent to 0.65 weight percent ketamine. The methods may comprise placing troche base into a chamber. The methods may comprise applying heat to the chamber. The heat may be sufficient to melt the troche base in the chamber. The methods may comprise adding a first ingredient into the chamber. The first ingredient may include ketamine. The methods may comprise mixing the first ingredient into the melted troche base in the chamber to form a melted mixture. The methods may comprise pouring the melted mixture into a mold. The methods may comprise cooling the melted mixture in the mold to form the lozenge.

20 Claims, 2 Drawing Sheets

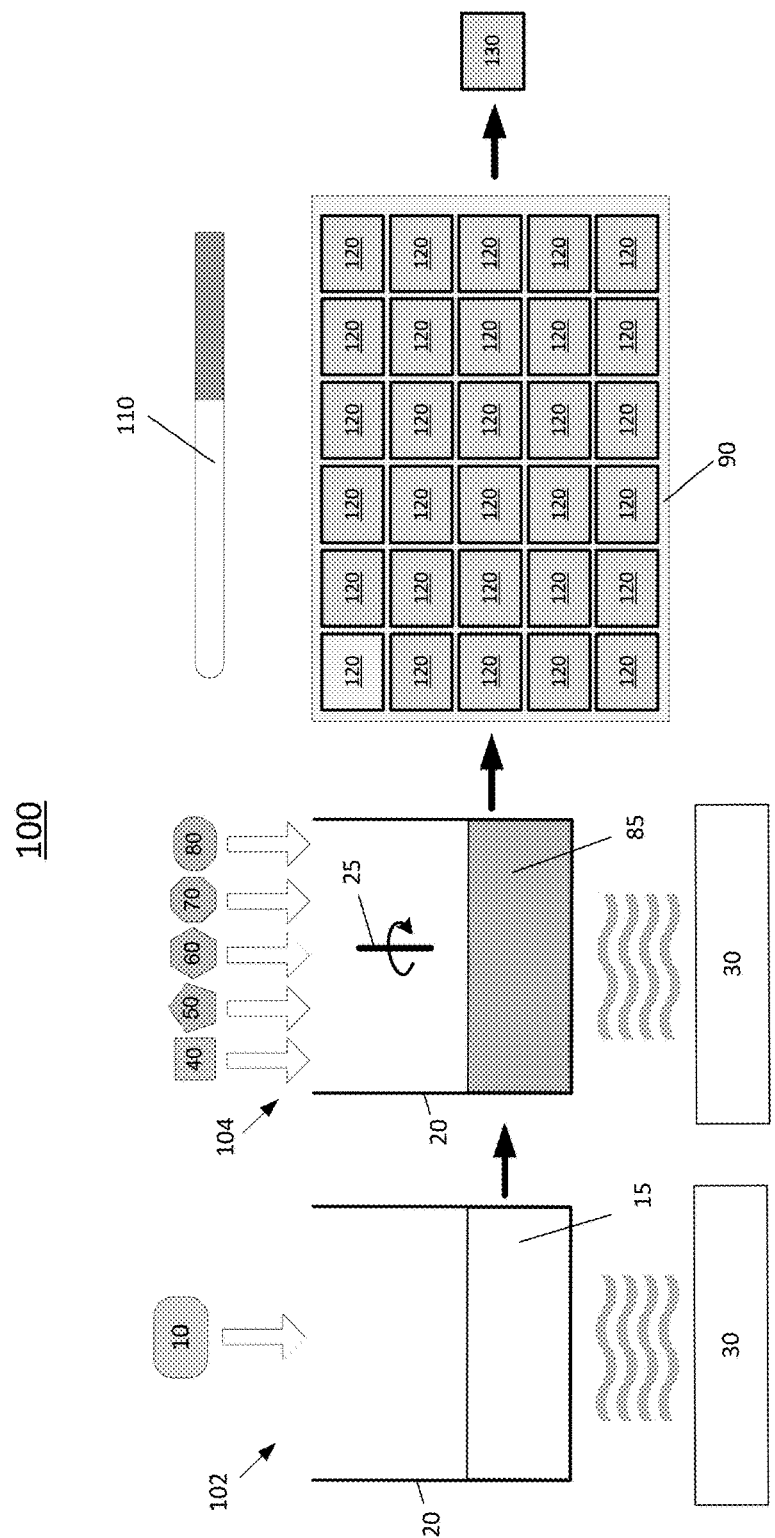

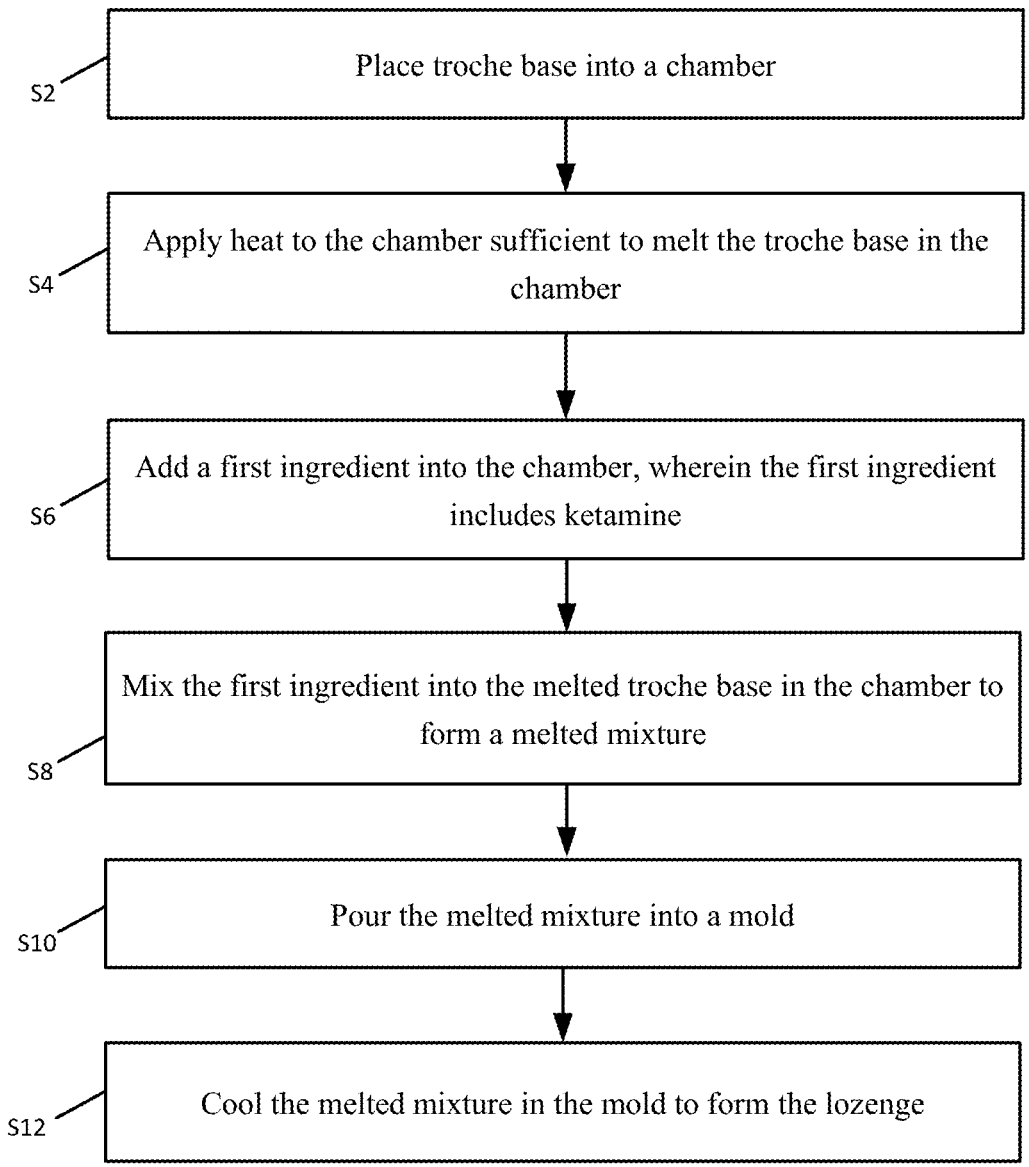

SUBLINGUAL ANTIDEPRESSANT LOZENGE

BACKGROUND

Antidepressant treatments may include therapies that target monoaminergic (MA) systems. Antidepressant treatments that target monoaminergic (MA) systems may require 4-6 weeks of administration to achieve effects, may include unpleasant side effects, may possess modest efficacy rates, and may display significant relapse rates. N-Methyl-D-aspartate (NMDA) receptor antagonists may be used as anesthetics and hallucinogenic recreational drugs. Ketamine, diethyl ether, dizocilpine, memantine, phencyclidine, nitrous oxide, and dextromethorphan may be MNDA receptor antagonists.

SUMMARY

In some examples lozenges are described. The lozenges may comprise troche base and ketamine. The lozenges may comprise 0.35 weight percent to 0.65 weight percent ketamine.

In some examples, methods to produce lozenges are described. The methods may comprise placing troche base into a chamber. The methods may comprise applying heat to the chamber. The heat may be sufficient to melt the troche base in the chamber. The methods may comprise adding a first ingredient into the chamber. The first ingredient may include ketamine. The methods may comprise mixing the first ingredient into the melted troche base in the chamber to form a melted mixture. The methods may comprise pouring the melted mixture into a mold. The methods may comprise cooling the melted mixture in the mold to form the lozenge.

In some examples lozenges are described. The lozenges may comprise troche base and ketamine. The lozenges may comprise 0.995 grams of troche base and 0.005 grams of ketamine.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 illustrates an example system that can be utilized to produce a sublingual antidepressant lozenge;

FIG. 2 illustrates a flow diagram of an example process to produce a sublingual antidepressant lozenge;

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system that can be utilized to produce a sublingual antidepressant lozenge, arranged in accordance with at least some embodiments presented herein. As discussed in more detail below, a sublingual antidepressant lozenge may be effective in the treatment of depression and anxiety.

System 100 may include a chamber 20, a heater 30 and a lozenge mold 90. At 102 a troche base 10 may be placed in within chamber 20 and melted by heat from heater 30 to produce melted troche base 15. Troche base 10 may be a blend of polyethylene glycols (PEGs). Troche base 10 may be white and/or translucent in appearance and be in the shape of small pellet pieces. Troche base 10 may be solid at room temperatures of 20 to 25 degrees Celsius. Heater 30 may supply heat to increase a temperature of troche base 10 to about 45 to 60 degrees Celsius and melt troche base 10 to produce melted troche base 15.

At 104, a mixing instrument 25 may be inserted into chamber 20 and ingredients 40, 50, 60 70, and 80 may each be individually and respectively added and blended into melted troche base 15. Mixing instrument 25 may be a manual mixing instrument such as a spoon or whisk, or an automated mixer.

Ingredient 40 may be in powder form. Ingredient 40 may include ketamine. Ingredient 40 may include ketamine hydrochloride (HCl) powder.

Ingredient 50 may be in powder form. Ingredient 50 may include silica gel powder. Ingredient 50 may be granular, vitreous in appearance, and porous. Ingredient 50 may be tough and hard in texture. Ingredient 50 may include a strong affinity for water molecules. Ingredient 50 may be silicon dioxide produced synthetically from sodium silicate. Ingredient 50 may have an average pore size of about 2.4 nanometers. Ingredient 50 may be a suspending agent and may keep materials from settling at the bottom of a mold cavity during cooling.

Ingredient 60 may be in powder form. Ingredient 60 may include a weak organic tribasic acid. Ingredient 60 may include citrate. Ingredient 60 may include citric acid powder. Ingredient 60 may include an acidifier, a flavoring, a chelating agent, or a pH adjusting agent. Ingredient 60 may include a processing aid.

Ingredient 70 may be in powder form. Ingredient 70 may include acacia powder. Ingredient 70 may include gum exuded from the acacia tree. Ingredient 70 may include dietary fiber that can dissolve in water. Ingredient 70 may add texture and smoothness to a sublingual antidepressant lozenge.

Ingredient 80 may be in liquid form. Ingredient 80 may be a liquid flavoring. Ingredient 80 may include a liquid confection product. Ingredient 80 may enhance digestion and taste of a sublingual antidepressant lozenge.

As shown at 104, ingredient 40 may be added to chamber 20 and blended into melted troche base 15. Ingredient 40 may be geometrically diluted into melted troche base 15. Ingredient 40 may be mixed until ingredient 40 is evenly distributed throughout melted troche base 15 as indicated by an even distribution of a color of ingredient 40 throughout melted troche base 15.

As shown at 104, ingredient 50 may be added to chamber 20 and blended into melted troche base 15. Ingredient 50 may be geometrically diluted into melted troche base 15. Ingredient 50 may be mixed until ingredient 50 is evenly distributed throughout melted troche base 15 as indicated by an even distribution of a color of ingredient 50 throughout melted troche base 15.

As shown at 104, ingredient 60 may be added to chamber 20 and blended into melted troche base 15. Ingredient 60 may be geometrically diluted into melted troche base 15. Ingredient 60 may be mixed until ingredient 60 is evenly distributed throughout melted troche base 15 as indicated by an even distribution of a color of ingredient 60 throughout melted troche base 15.

As shown at 104, ingredient 70 may be added to chamber 20 and blended into melted troche base 15. Ingredient 70 may be geometrically diluted into melted troche base 15. Ingredient 70 may be mixed until ingredient 70 is evenly distributed throughout melted troche base 15 as indicated by an even distribution of a color of ingredient 70 throughout melted troche base 15.

As shown at 104, ingredient 80 may be added to chamber 20 and blended into melted troche base 15. Ingredient 80 may be mixed until ingredient 80 is evenly distributed throughout melted troche base 15 as indicated by an even distribution of a color of ingredient 80 throughout melted troche base 15.

A melted lozenge mixture 85 may be formed by mixing ingredients 40, 50, 60 70, and 80 into melted troche base 15. Melted lozenge mixture 85 may be poured into cavities 120 of lozenge mold 90. Lozenge mold 90 may be plastic, anodized aluminum, or some other non-permeable material, and may be configured to form equal sized lozenges. Lozenge mold 90 may include 30 uniformly sized cavities 120. Melted lozenge mixture 85 may be poured into cavities 120 of lozenge mold 90 so as to completely fill cavities 120. A scrapper or spatula 110 may be used to level and even out poured melted lozenge mixture 85 in cavities 120 of lozenge mold 90. Spatula 110 may also be used to wipe any excess melted lozenge mixture 85 off of lozenge mold 90.

Lozenge mold 90, with cavities 120 filled with melted lozenge mixture 85, may be cooled to room temperature of 20 to 25 degrees Celsius to form lozenge 130. Lozenge 130 may be a solid lozenge with ingredients 40, 50, 60, 70, and 80 distributed evenly throughout lozenge 130. Lozenge 130 may include about 0.35 weight percent to about 0.65 weight percent of ingredient 40. Lozenge 130 may include about 1.05 weight percent to about 1.35 weight percent of ingredient 50. Lozenge 130 may include about 1.20 weight percent to about 1.55 weight percent of ingredient 60. Lozenge 130 may include about 1.80 weight percent to about 2.10 weight percent of ingredient 70.

Example 1

Lozenge 130 may include:

0.5 weight percent of ingredient 40;
1.2 weight percent of ingredient 50;
1.38 weight percent of ingredient 60; and
1.98 weight percent of ingredient 70.

Example 2

A mold with 30 uniformly sized cavities may be utilized to mold 30 lozenges 130 from melted lozenge mixture 85 formed from the following quantities:

melted lozenge mixture 85 formed from the following quantities:
0.150 grams of ingredient 40. Ingredient 40 may be ketamine HCl powder.
0.360 grams of ingredient 50. Ingredient 50 may be silica gel powder.
0.414 grams of ingredient 60. Ingredient 60 may be citric acid powder.
0.594 grams of ingredient 70. Ingredient 70 may be acacia powder.
29.850 grams of troche base 10.

6.000 ml of ingredient 80. Ingredient 80 may be tutti frutti flavor liquid.

Example 3

Lozenge 130 may be formed from the following quantities:

0.005 grams of ingredient 40. Ingredient 40 may be ketamine HCl powder.
0.012 grams of ingredient 50. Ingredient 50 may be silica gel powder.
0.0138 grams of ingredient 60. Ingredient 60 may be citric acid powder.
0.0198 grams of ingredient 70. Ingredient 70 may be acacia powder.
0.995 grams of troche base 10.
0.200 ml of ingredient 80. Ingredient 80 may be tutti frutti flavor liquid.

FIG. 2 illustrates a flow diagram of an example process to produce a sublingual antidepressant lozenge 130. The process in FIG. 2 could be implemented using, for example, system 100 discussed above. An example process may include one or more operations, actions, or functions as illustrated by one or more of blocks S2, S4, S6, S8, and/or S10. Although illustrated as discrete blocks, various blocks may be divided into additional blocks, combined into fewer blocks, or eliminated, depending on the desired implementation.

Processing may begin at block S2, "Place troche base into a chamber." At block S2, a troche base may be placed into a chamber. The troche base may be a blend of polyethylene glycols (PEGs). The troche base may be white and/or translucent in appearance and be in the shape of small pellet pieces. The troche base may be solid at room temperatures of 20 to 25 degrees Celsius.

Processing may continue from block S2 to block S4, "Apply heat to the chamber sufficient to melt the troche base in the chamber." At block S4, heat may be applied to the chamber sufficient to melt the troche base. Heat may be applied to the chamber sufficient to increase a temperature of the troche base to about 45 to 60 degrees Celsius and melt the troche base.

Processing may continue from block S4 to block S6, "Add a first ingredient into the chamber, wherein the first ingredient includes ketamine." At block S6, a first ingredient may be added to the chamber. The first ingredient may include ketamine. The first ingredient may include ketamine hydrochloride (HCl) powder.

Processing may continue from block S6 to block S8, "Mix the first ingredient into the melted troche base in the chamber to form a melted mixture." At block S8, the first ingredient may be mixed into the melted troche base in the chamber. The mixing may be performed by a manual mixing instrument such as a spoon or whisk, or an automated mixer. The first ingredient may be mixed until the first ingredient is evenly distributed throughout the melted troche base as indicated by an even distribution of a color of the first ingredient throughout the melted troche base.

Processing may continue from block S8 to block S10, "Pour the melted mixture into a mold." At block S10, the melted mixture may be poured into a mold. The mold may be plastic, anodized aluminum, or some other non-permeable material. The mold may be configured with cavities to form uniform sized lozenges. The melted mixture may be poured into the cavities of the mold. The melted mixture may be poured into the cavities of the mold so as to completely fill the cavities of the mold. A scrapper or spatula may be used to level and even out poured melted mixture in the cavities of the mold. The spatula may also be used to wipe any excess melted mixture off of the mold.

Processing may continue from block S10 to block S12, "Cool the melted mixture in the mold to form the lozenge." At block S12, the melted mixture in the mold may be cooled to form the lozenge. The melted mixture may be cooled to room temperature of 20 to 25 degrees Celsius.

A system in accordance with the present disclosure may be effective to produce a sublingual antidepressant lozenge. A potential benefit of the present application may be the treatment of depression effects in treatment-resistant depression. An embodiment of the present application may provide a more rapid effect than antidepressant treatments which include therapies that target monoaminergic (MA) systems and require 4-6 weeks of administration to achieve effects. An embodiment of the present application may provide a higher efficacy rate than therapies that target monoaminergic (MA) systems.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An antidepressant lozenge comprising a troche base and 0.35 weight percent to 0.65 weight percent ketamine, wherein the antidepressant lozenge is a treatment for depression and anxiety.

2. The lozenge of claim 1, further comprising 1.05 weight percent to 1.35 weight percent silica gel powder.

3. The lozenge of claim 1, further comprising 1.2 weight percent to 1.55 weight percent citric acid powder.

4. The lozenge of claim 1, further comprising 1.8 weight percent to 2.1 weight percent acacia powder.

5. The lozenge of claim 1, further comprising:

1.05 weight percent to 1.35 weight percent silica gel powder;
1.2 weight percent to 1.55 weight percent citric acid powder; and
1.8 weight percent to 2.1 weight percent acacia powder.

6. The lozenge of claim 5, comprising:

0.5 weight percent ketamine;
1.2 weight percent silica gel powder;
1.38 weight percent citric acid powder; and
1.98 weight percent acacia powder.

7. The lozenge of claim 5, further comprising a liquid flavoring.

8. The lozenge of claim 1, wherein the troche base includes a blend of polyethylene glycols.

9. The lozenge of claim 1, wherein the ketamine includes ketamine hydrochloride powder.

10. A method to produce an antidepressant lozenge, the method comprising:

placing troche base into a chamber;
applying heat to the chamber sufficient to melt the troche base in the chamber;
adding a first ingredient into the chamber, wherein the first ingredient includes ketamine;
mixing the first ingredient into the melted troche base in the chamber to form a melted mixture;
pouring the melted mixture into a mold; and
cooling the melted mixture in the mold to form the antidepressant lozenge, wherein the antidepressant lozenge is a treatment for depression and anxiety.

11. The method of claim 10, further comprising, prior to pouring the melted mixture into the mold:

adding a second ingredient to the chamber, wherein the second ingredient includes silica gel powder; and
mixing the second ingredient with the melted mixture in the chamber.

12. The method of claim 10, further comprising, prior to pouring the melted mixture into the mold:

adding a second ingredient to the, wherein the second ingredient includes citric acid powder; and
mixing the second ingredient with the melted mixture in the chamber.

13. The method of claim 10, further comprising, prior to pouring the melted mixture into the mold:

adding a second ingredient to the chamber, wherein the second ingredient includes acacia powder; and
mixing the second ingredient with the melted mixture in the chamber.

14. The method of claim 10, further comprising, prior to pouring the melted mixture into the mold:

adding a second ingredient to the chamber, wherein the second ingredient includes silica gel powder;
mixing the second ingredient with the melted mixture in the chamber;
adding a third ingredient to the chamber, wherein the third ingredient includes citric acid powder;
mixing the third ingredient with the melted mixture in the chamber;
adding a fourth ingredient to the chamber, wherein the fourth ingredient includes acacia powder; and
mixing the fourth ingredient with the melted mixture in the chamber.

15. The method of claim 14, further comprising, prior to pouring the melted mixture into the mold:

adding a liquid flavoring to the chamber; and
mixing the liquid flavoring with the melted mixture in the chamber.

16. The method of claim 15, wherein:

the mold includes thirty uniformly sized cavities;
the troche base weighs 29.850 grams;
the ketamine weighs 0.150 grams;
the silica gel powder weighs 0.360 grams;
the citric acid powder weighs 0.414 grams;
the acacia powder weighs 0.594 grams; and
a quantity of the liquid flavor is 6.000 ml.

17. The method of claim 10, wherein the ketamine includes ketamine hydrochloride powder.

18. An antidepressant lozenge comprising 0.995 grams of troche base and 0.005 grams of ketamine, wherein the antidepressant lozenge is a treatment for depression and anxiety.

19. The lozenge of claim 18, wherein the troche base includes a blend of polyethylene glycols and the ketamine includes ketamine hydrochloride powder.

20. The lozenge of claim 18, further comprising:

0.012 grams of silica gel powder;
00.0138 grams of citric acid powder; and
0.0198 grams of acacia powder.

\* \* \* \* \*